United States Patent [19]

Davison et al.

[11] Patent Number: 4,879,303

[45] Date of Patent: Nov. 7, 1989

[54] PHARMACEUTICALLY ACCEPTABLE SALTS

[75] Inventors: Edward Davison, Margate; James I. Wells, Canterbury, both of England

[73] Assignee: Pfizer Inc., New York, N.Y.

[21] Appl. No.: 256,938

[22] Filed: Oct. 13, 1988

Related U.S. Application Data

[63] Continuation of Ser. No. 30,658, Mar. 25, 1987, abandoned.

[30] Foreign Application Priority Data

Apr. 4, 1986 [GB] United Kingdom ................. 8608335

[51] Int. Cl.$^4$ .................. C07D 211/86; A61K 31/455
[52] U.S. Cl. ...................................... 514/356; 546/321
[58] Field of Search .......................... 514/356; 546/321

[56] References Cited

U.S. PATENT DOCUMENTS 3,816,612 6/1974 Schmidt et al. ....................... 425/45
4,032,637 6/1977 Spiegel et al. ....................... 514/224

OTHER PUBLICATIONS

Berge et al., Jour. of Pharmaceutical Science, Jan. 1977, vol. 66, No. 1.

Primary Examiner—Jane T. Fan
Attorney, Agent, or Firm—Peter C. Richardson; J. Trevor Lumb; James M. McManus

[57] ABSTRACT

Improved pharmaceutical salts of amlodipine, particularly the besylate salt, and pharmaceutical compositions thereof. These salts find utility as anti-ischaemic and anti-hypertensive agents.

11 Claims, No Drawings

PHARMACEUTICALLY ACCEPTABLE SALTS

This application is a continuation application of co-pending application Ser. No. 07/030,658, filed Mar. 25, 1987, now abandoned.

BACKGROUND OF THE INVENTION

The present invention relates to improved pharmaceutical salts of amlodipine and pharmaceutical compositions thereof.

The compound amlodipine (3-ethyl 5-methyl 2-(2-aminoethoxymethyl)-4-(2-chlorophenyl)-1,4-dihydro-6-methylpyridine-3,5-dicarboxylate) is a potent and long acting calcium channel blocker having utility as an anti-ischaemic and anti-hypertensive agent.

European Patent Application Publication No. 89167 and U.S. Pat. No. 4,572,909 disclose several different pharmaceutically acceptable salt forms of amlodipine. In particular, the pharmaceutically acceptable acid addition salts are said to be those formed from acids which form non-toxic acid anions such as the hydrochloride, hydrobromide, sulphate, phosphate or acid phosphate, acetate, maleate, fumarate, lactate, tartrate, citrate and gluconate salts. Of these salts the maleate is disclosed as being particularly preferred.

SUMMARY OF THE INVENTION

It has now unexpectedly been found that the benzene sulphonate salt (hereinafter referred to as the besylate salt) has a number of advantages over the known salts of amlodipine and, additionally, has unexpectedly been found to have a unique combination of good formulation properties which make it particularly suitable for the preparation of pharmaceutical formulations of amlodipine.

Thus according to the present invention there is provided the besylate salt of amlodipine.

In a further aspect the invention provides a pharmaceutical composition of the besylate salt of amlodipine together with a pharmaceutically acceptable diluent or carrier.

The invention further provides a tablet formulation comprising the besylate salt of amlodipine in admixture with excipients. A preferred formulation includes the besylate salt, a compression aid such as microcrystalline cellulose, an additive to provide sheen to the table such as anhydrous dibasic calcium phosphate, a disintegrant such as sodium starch glycollate and a lubricant such as magnesium stearate.

In addition the invention provides a capsule formulation comprising the besylate salt of amlodipine in admixture with excipients. A preferred formulation includes the besylate salt, an inert diluent, a dried disintegrant and a lubricant as described above.

The invention further provides the besylate salt of amlodipine in sterile aqueous solution for parenteral administration. Preferably such solution contains from 10 to 40% by volume of propylene glycol and preferably also sufficient sodium chloride to avoid haemolysis, e.g. about 1% w/v.

The invention also provides the besylate salt of amlodipine for use in treating ischaemic heart disease, especially angina, or hypertension, in a human being.

The invention also provides a process for preparing the besylate salt of amlodipine by reacting amlodipine base with a solution of benzenesulphonic acid in an inert solvent and recovering the besylate salt of amlodipine.

The preferred inert solvent is industrial methylated spirit.

DETAILED DESCRIPTION OF THE INVENTION

Although amlodipine is effective as the free base, in practice it is best administered in the form of a salt of a pharmaceutically acceptable acid. In order to be suitable for this purpose the pharmaceutically acceptable salt must satisfy the following four physiochemical criteria: (1) good solubility; (2) good stability; (3) non-hydroscopicity; (4) processability for tablet formulation, etc.

It has been found that whilst many of the salts outlined above satisfy some of these criteria, none satisfy them all and even the preferred maleate, whilst exhibiting excellent solubility tends to break-down in solution after a few weeks. Consequently a range of pharmaceutically acceptable salts of amlodipine has been made and evaluated using these criteria:

1. Generally, it is known in the art that a good aqueous solubility is necessary for good bioavailability. Usually a solubility of greater than 1 mg ml$^{-1}$ at pH 1-7.5 is sought although higher solubilities are required to formulate injections. In addition, salts which provide solutions having a pH close to that of blood (7.4) are preferred because they are readily biocompatible and can easily be buffered to the required pH range without altering their solubility.

As can be seen from the following comparative data the besylate salt of amlodipine exhibits good solubility characteristics, compared with other salts.

TABLE 1

| Salt | solubility mg ml$^{-1}$ | pH at saturation |
| --- | --- | --- |
| Benzene sulphonate (besylate) | 4.6 | 6.6 |
| Toluene sulphonate (tosylate) | 0.9 | 5.9 |
| Methane sulphonate (mesylate) | 25 | 3.1 |
| Succinate | 4.4 | 4.9 |
| Salicylate | 1.0 | 7.0 |
| Maleate | 4.5 | 4.8 |
| Acetate | 50 | 6.6 |
| Hydrochloride | 50 | 3.5 |

2. Good stability in the solid state is very important for tablets and capsules, whilst good stability in solution is required for an aqueous injection.

In order to screen for chemical stability, each of the salts was blended in a powder vehicle and formed into tablets or capsules. In the case of tablets the vehicle comprised microcrystalline cellulose in 50:50 combination with anhydrous dibasic calcium phosphate. In the case of capsules the vehicles comprised mannitol in 4:1 combination with dried maize starch. These were then stored in sealed vials at 50° and 75° C. for up to three weeks. The drug and any breakdown products were extracted with methanol:chloroform (50:50) and separated on silica tlc plates using a variety of solvent systems.

The results were compared and the salts ranked according to the number and amount of breakdown product produced.

By comparing the results the following rank order emerges with besylate being the most stable salt and hydrochloride the least stable.

| Salt | Stability |
|---|---|
| Besylate | most stable |
| Mesylate | ↓ |
| Tosylate | ↓ |
| Succinate | ↓ |
| Salicylate | ↓ |
| Maleate | ↓ |
| Acetate | ↓ |
| Hydrochloride | unstable |

3. In order to provide stable formulations it is desirable to have a non-hygroscopic salt. In the solid state where drug content is high, absorbed films of moisture can act as a vector for hydrolysis and chemical breakdown. It is the hygroscopic nature of a drug or its salt which contributes to the free moisture which is normally responsible for instability.

Only the maleate, tosylate and besylate salts do not pick up any moisture when exposed to 75% relative humidity at 37° C. for 24 hours. Even when exposed to 95% relative humidity at 30° C. for 3 days both the besylate and maleate remain anhydrous whilst the tosylate formed the dihydrate salt. Therefore the besylate salt can be considered to be non-hygroscopic and thus provides stale formulations while minimising the risk of intrinsic chemical breakdown.

4. The final characteristic of an acceptable salt to be considered is the processability, i.e. the compression properties and also the ability not to stick or adhere to the tablet making machinery.

For high dose formulations, good compressibility is very important to make elegant tablets. With lower dose tablets the need for good compressibility can be eliminated to a certain extent by the use of suitable diluting excipients called compression aids. Microcrystalline cellulose is a commonly used compression aid. However whatever the dose the adhesion of the drug to the punches of the tablet machine must be avoided. When drug accumulates on the punch surfaces this causes the tablet surface to become pitted and therefore unacceptable. Also sticking of the drug in this way results in high ejection forces when removing the tablet from the machine. In practice it is possible to reduce sticking by wet-massing, careful selection of excipients and the use of high levels of anti-adherents, e.g. magnesium stearate. However selection of a salt with good anti-adhesion properties minimises these problems.

In order to compare the stickiness of the various salts of amlodipine the following procedure was carried out using conventional tablet making machinery: fifty tablets containing calcium sulphate dihydrate, microcrystalline cellulose and amlodipine besylate were made (47.5:47.5:5), the material sticking to the tablet punch was then extracted using methanol and the amount measured spectrometrically. This procedure was then repeated for runs of 100, 150, 200, 250 and 300 tables. After each run the amount of material sticking to the tablet punch was measured after extraction with methanol. The values are plotted and an average value calculated from the slope of the line produced.

This same procedure was then repeated for each of the salts of amlodipine. The amount of amlodipine measured as sticking to the tablet punch is shown in Table 2 for each salt and relative to the maleate salt.

TABLE 2

| Salt | Stickiness g Amlodipine cm$^{-2}$ tablet$^{-1}$ | Relative to maleate |
|---|---|---|
| Mesylate | 1.16 | 58% |
| Besylate | 1.17 | 59 |
| Tosylate | 1.95 | 98 |
| Maleate | 1.98 | 100 |
| Free base | 2.02 | 102 |
| Succinate | 2.39 | 121 |
| Hydrochloride | 2.51 | 127 |
| Salicylate | 2.85 | 144 |

Clearly the besylate has superior anti-adhesion properties to the maleate. Whilst the mesylate also shows good processability it tends to be isolated as the anhydride but this equilibrates to the monohydrate leading to variable composition after manufacture which makes it unacceptable for use in tablets.

Thus the besylate salt of amlodipine shows a unique combination of good solubility, good stability, non-hygroscopicity and good processability which makes it outstandingly suitable for the preparation of pharmaceutical formulations of amlodipine.

In order that the present invention be more readily understood, reference is now made to the following Examples.

EXAMPLE 1

Preparation of Besylate Salt of Amlodipine

Amlodipine base (65.6 g, 0.161 mols) was slurried in industrial methylated spirit (326.4 ml) and cooled to 5° C. Benzenesulphonic acid (26.2 g, 0.168 mols) was dissolved in industrial methylated spirit (65.6 ml) at 5° C. and added to the slurry of the base. The resulting slurry was then granulated, filtered and washed with 2 volumes of industrial methylated spirit (65.6 ml). The damp solid was slurried at 5° C. for 1 hr in industrial methylated spirit (327.6 ml), filtered, washed with 2 volumes of industrial methylated spirit (65.6 ml) and dried under vacuum at 55° C. for 24 hours. A yield of 6.5 g (83.8%) was obtained with the following analysis.

| Analysis % | Melting Point 201.0° C. | | |
|---|---|---|---|
| | C | H | N |
| Calc. | 55.07 | 5.51 | 4.94 |
| Found | 54.91 | 5.46 | 4.93 |

EXAMPLE 2

Formulation of Tablets Containing Besylate Salt of Amlodipine

Amlodipine besylate was blended with sodium starch glycollate and anhydrous dibasic calcium phosphate for 5 minutes. This mixture was then sieved, reblended and sieved again followed by blending with microcrystalline cellulose. The resultant mixture was then sieved again and blended for a further 10 minutes. Finally magnesium stearate was added and the whole mixture blended for 5 minutes. The blend was then pressed into tablets using conventional tablet making machinery.

TABLE 3

TABLET COMPOSITIONS

| Besylate salt (mg) | Microcrystalline cellulose (mg) | Anhydrous dibasic calcium phosphate (mg) | Sodium starch glycollate (mg) | Magnesium stearate (mg) |
|---|---|---|---|---|
| 1.736 | 63.514 | 31.750 | 2.00 | 1.00 |
| 3.472 | 62.028 | 31.500 | 2.00 | 1.00 |
| 6.944 | 124.056 | 63.000 | 4.00 | 2.00 |
| 13.889 | 248.111 | 126.000 | 8.00 | 4.00 |

This method was used to make tablets containing different concentrations of the amlodipine besylate salt as shown in table 3.

EXAMPLE 3

Formulation of Capsules Containing Besylate Salt of Amlodipine

Microcrystalline cellulose and dried maize starch were preblended. The besylate salt of amlodipine was then mixed with some of this preblend and then sieved. The remainder of the preblend was then added and mixed for 10 minutes. This was then sieved again and mixed for a further 5 minutes.

This method was used to make mixtures containing different concentrations of the amlodipine besylate salt as shown in Table 4 and the mixtures were then filled into capsules of appropriate size.

TABLE 4

CAPSULE COMPOSITIONS

| Besylate salt (mg) | Microcrystalline cellulose (mg) | Dried Maize starch (mg) | Magnesium stearate (mg) | Total Capsule weight (mg) |
|---|---|---|---|---|
| 1.736 | 38.014 | 10.00 | 0.250 | 50 |
| 3.472 | 76.028 | 20.00 | 0.500 | 100 |
| 6.944 | 72.556 | 20.00 | 0.500 | 100 |
| 13.889 | 145.111 | 40.00 | 1.00 | 200 |

EXAMPLE 4

Formulation of Sterile Aqueous Solution of Besylate Salt of Amlodipine

Sodium chloride was dissolved in water for injection and propylene glycol was mixed with this solution. The besylate salt of amlodipine was added and, when it has dissolved, further water for injection was added to adjust the volume to give the desired concentration of amlodipine (1 mg/ml). The solution was then filtered through a sterilising filter and filled into suitable sterile containers, e.g. ampoules, for use in parenteral, e.g. intravenous, administration.

This methods was used to prepare the formulations shown in Table 5.

TABLE 5

STERILE AQUEOUS SOLUTIONS

| | (1) | (2) |
|---|---|---|
| Besylate salt of amlodipine | 1.389 g | 1.389 g |
| Sodium chloride | 9.000 g | 9.000 g |
| Propylene glycol | 200.000 g | 400.000 g |
| Water for injection | to 1 liter | to 1 liter |

EXAMPLE 5

Alternative preparation of Besylate salt of Amlodipine

Ammonium benzenesulphonate (0.943 g) was added to a slurry of amlodipine base (2 g) in industrial methylated spirit (10ml) and the resulting solution was heated at reflux for 10 minutes. The reaction mixture was cooled and granulated at 5° C. for 1 hour. The amlodipine benzenesulphonate was filtered, washed with industrial methylated spirit (2×2 ml) and dried in vacuum.

Yield 1.9 g (70% of theory).
Mpt.: 201.0° C.

| Mpt.: 201.0° C. | |
|---|---|
| Analysis % | |
| Found | C, 54.98; H, 5.46; N, 4.90; |
| Calculated for | C, 55.07; H, 5.51; N, 4.95. |

We claim:

1. The besylate salt of amlodipine.
2. A pharmaceutical composition comprising an antihypertensive, antiischaemic or angina - alleviating effective amount of the besylate salt of amlodipine as claimed in claim 1 together with a pharmaceutically acceptable diluent or carrier.
3. A tablet formulation comprising an anti-hypertensive, antiischaemic or angina - alleviating effective amount of the besylate salt of amlodipine as claimed in claim 1 in admixture with excipients.
4. A tablet formulation as claimed in claim 3 wherein the excipients comprise a compression and, an additive to provide sheen to the tablet, a disintegrant and a lubricant.
5. A tablet formulation as claimed in claim 4 wherein the excipients comprise microcrystalline cellulose, anhydrous dibasic calcium phosphate, sodium starch glycollate and magnesium stearate.
6. A capsule formulation comprising an antihypertensive, antiischaemic or angina - alleviating effective amount of the besylate salt of amlodipine as claimed in claim 1 in admixture with excipients.
7. A capsule formulation as claimed in claim 6 wherein the excipients comprise an inert diluent, a dried disintegrant and a lubricant.
8. A capsule formulation as claimed in claim 7 wherein the excipients comprise microcrystalline cellulose, dried maize starch and magnesium stearate.
9. A sterile aqueous solution comprising an antihypertensive, antiischaemic or angina - alleviating effective amount of the besylate salt of amlodipine for parenteral administration.
10. A sterile aqueous solution as claimed in claim 9 comprising from 10 to 40% w/v of propylene glycol.
11. A sterile aqueous solution as claimed in claim 9 or claim 10 comprising about 1% w/v sodium chloride.

* * * * *